United States Patent [19]

Worthington et al.

[11] 4,289,526

[45] Sep. 15, 1981

[54] HETEROCYCLIC COMPOUNDS, PROCESSES FOR THEIR PREPARATION, PESTICIDAL COMPOSITIONS CONTAINING THEM AND METHODS OF COMBATING PESTS

[75] Inventors: Paul A. Worthington, Maidenhead; Paul de Fraine; William G. Rathmell, both of Workingham; Diana M. Gatehouse, Maidenhead, all of England

[73] Assignee: Imperial Chemical Industries Limited, London, England

[21] Appl. No.: 161,558

[22] Filed: Jun. 20, 1980

[30] Foreign Application Priority Data

Jul. 12, 1979 [GB] United Kingdom ............... 24302/79

[51] Int. Cl.$^3$ .................... A61K 31/41; A61K 31/555; C07D 405/04; C07F 15/02

[52] U.S. Cl. ........................................ 71/92; 424/245; 424/269; 424/273 R; 548/101; 548/262; 548/336; 564/256

[58] Field of Search ...................... 548/262, 101, 336; 424/245, 269, 273 R; 71/92

[56] References Cited

U.S. PATENT DOCUMENTS

| | | | |
|---|---|---|---|
| 4,101,665 | 7/1978 | Heeres | 548/341 |
| 4,217,129 | 8/1980 | Shephard et al. | 548/262 |

*Primary Examiner*—Alton D. Rollins
*Attorney, Agent, or Firm*—Cushman, Darby & Cushman

[57] ABSTRACT

This invention relates to imidazole and triazole compounds useful as fungicides, herbicides and plant growth regulators; to a process for preparing them; to compositions containing them; and to methods of using them to combat fungal infections in plants and to control the growth of vegetation.

7 Claims, No Drawings

HETEROCYCLIC COMPOUNDS, PROCESSES FOR THEIR PREPARATION, PESTICIDAL COMPOSITIONS CONTAINING THEM AND METHODS OF COMBATING PESTS

The invention provides compounds having the general formula (I)

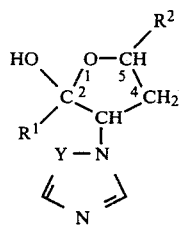

wherein each of $R^1$ and $R^2$, which may be the same or different, is unsubstituted or alkyl-substituted cycloalkyl, unsubstituted or halo-substituted alkyl or unsubstituted or substituted phenyl, Y is =N- or =CH-; and esters, ethers, acid addition salts and metal complexes thereof; and any isomer of the foregoing.

The compounds of the invention contain 3-chiral centres based on the 2, 3 and 5 ring positions of the tetrahydrofuran ring. The compounds are generally obtained in the form of racemic mixtures. However, these and other mixtures can be separated into the individual isomers by methods known in the art e.g. chromatography. In many cases, the compounds can be prepared stereo-specifically in the form of single diastereoisomer.

The alkyl groups, which can be straight or branched chain, preferably have 1 to 5 carbon atoms; examples are methyl, ethyl, propyl (n- or i-propyl) and butyl (n-, i- or t-butyl).

Suitable substituents (preferred substituents are asterisked) for the phenyl group are halogen,* $C_{1-4}$ alkyl* [e.g. methyl, ethyl, propyl (n- or i-propyl) and butyl (n-, or i- or t-butyl)], halo $C_{1-4}$ alkyl* (e.g. chloro- or bromomethyl), hydroxy $C_{1-4}$ alkyl* (e.g. hydroxymethyl), phenyl,* halophenyl* (e.g. chlorophenyl), cycloalkyl,* nitro,* cyano,* $C_{1-4}$ alkoxy* (e.g. methoxy, ethoxy, propoxy or butoxy), $C_{2-4}$ alkenyloxy (e.g. allyloxy), ($C_{1-4}$ alkylene)dioxy (e.g. methylenedioxy), ($C_{1-4}$ alkoxy) ($C_{1-4}$ alkyl) [e.g. methoxy- or ethoxymethyl or 2-methoxy- or ethoxy-ethyl], mercapto, ($C_{1-4}$ alkyl)thio [e.g. methyl- or ethyl-thio], ($C_{1-4}$ alkyl)sulphonyl [e.g. methyl- or ethyl-sulphonyl], ($C_{1-4}$ haloalkyl)sulphonyl [e.g. trifluoromethylsulphonyl], phenylsulphonyl, unsubstituted or mono- or di- ($C_{1-4}$ alkyl) substituted sulphamoyl or carbamoyl, 1- pyrrolidinylsulphonyl, carboxy, ($C_{1-4}$ alkoxy)carbonyl [e.g. methoxy- or ethoxycarbonyl], hydroxy,* $C_{1-6}$ alkanoyloxy, benzoyloxy, carboxy ($C_{1-4}$ alkyl)oxy (e.g. carboxymethoxy or 1-carboxyethoxy), unsubstituted or mono- or di- ($C_{1-4}$ *alkyl*) *substituted amino*,* ($C_{1-6}$ alkanoyl)amino, formylamino, N-($C_{1-4}$ alkyl) formylamino, phenylethyl, methylene-dioxyphenyl, phenoxy* or benzyloxy.* A suitable alkanoyl is acetyl or propionyl. The phenyl group can have more than one substituent; examples of polysubstituted groups are those substituted with up to the maximum possible number (especially 1, 2 or 3) of for example halogen (particularly chlorine) atoms and/or nitro, methyl or methoxy groups.

Examples of suitable phenyl groups are phenyl itself, chlorophenyl (for example o-, m-, or p-chlorophenyl), dichlorophenyl (e.g. 3,4-, 2,4-, 3,5- or 2,6-dichlorophenyl), trichlorophenyl (e.g. 2,3,6- or 2,4,5-trichlorophenyl), tetrachlorophenyl, pentachlorophenyl, bromophenyl (e.g. o-, m- or p-bromophenyl), dibromophenyl (e.g. 2,4-dibromophenyl), fluorophenyl (e.g. o-, m- or p-fluorophenyl), difluorophenyl (e.g. 2,4- or 3,4-difluorophenyl), pentafluorophenyl, iodophenyl (e.g. o-iodophenyl), aminophenyl (e.g. p-aminophenyl), methylphenyl (e.g. o-, m- or p-methylphenyl), dimethylphenyl (e.g. 2,6-, 2,5- or 3,4-dimethylphenyl), ethylphenyl (e.g. p-ethylphenyl), propylphenyl (e.g. p-i-propylphenyl), butylphenyl (e.g. p-t-butylphenyl), cyanophenyl (e.g. o-, m-, or p-cyanophenyl), nitrophenyl (e.g. o-, m- or p-nitrophenyl), dinitrophenyl (e.g. 2,4-dinitrophenyl), cyanochlorophenyl (e.g. 3-cyano-4-chlorophenyl or 4-cyano-3-chlorophenyl), methylsulphonylphenyl (e.g. p-methylsulphonylphenyl), sulphamoylphenyl (e.g. p-sulphamoylphenyl), N,N-dimethylsulphamoylphenyl [e.g. p-(N,N-dimethylsulphamoyl)phenyl], pyrrolidin-1-ylsulphonylphenyl (e.g. p-pyrrolidin-1-ylsulphonylphenyl), trifluoromethylsulphonylphenyl (e.g. p-trifluoromethylsulphonylphenyl), methylthiophenyl (e.g. p-methylthiophenyl), (chloromethyl)phenyl [e.g. o-, m- or p-(chloromethyl)phenyl], (bromomethyl)phenyl [e.g. o-, m- or p-(bromomethyl)phenyl], (hydroxymethyl)phenyl [e.g. o-, m- or p-(hydroxymethyl)phenyl], (methoxymethyl)phenyl [e.g. o-, m- or p-(methoxymethyl)phenyl], carboxyphenyl (e.g. o-, m- or p-carboxyphenyl), methoxycarbonylphenyl (e.g. o-, m- or p-methoxycarbonylphenyl), N,N-dimethyl-carbamoylphenyl [e.g. o-, m- or p-(N,N-dimethylcarbamoyl)phenyl], N,N-dimethylaminophenyl [e.g. o-, m- or p-(N,N-dimethylamino)phenyl], hydroxyphenyl (e.g. o-, m- or p-hydroxyphenyl), acetoxyphenyl (e.g. o-, m-, or p-acetoxyphenyl), benzoyloxyphenyl (e.g. o-, m- or p-benzoyloxyphenyl), (trifluoromethyl)phenyl [e.g. o-, m- or p-(trifluoromethyl)phenyl], methoxyphenyl (e.g. o-, m- or p-methoxyphenyl), dimethoxyphenyl (e.g. 2,4-, 3,4- or 3,5-dimethoxyphenyl), ethoxyphenyl (e.g. o-, m- or p-ethoxyphenyl), propoxyphenyl (e.g. p-i-propoxyphenyl or p-n-propoxyphenyl), butoxyphenyl (e.g. o-, m- or p-i-butoxyphenyl), allyloxyphenyl (e.g. o-, m- or p-allyloxyphenyl), carboxymethoxyphenyl (e.g. o-, m- or p-carboxymethoxyphenyl), 1-carboxyethylphenyl [e.g. o-, m- or p-(1-carboxyethyl)phenyl], chloronitrophenyl (e.g. 3-nitro-4-chlorophenyl), fluoronitrophenyl (e.g. 2-nitro-4-fluorophenyl), chlorofluorophenyl (e.g. 2-fluoro-4-chlorophenyl, 2-chloro-6-fluorophenyl or 2-chloro-4-fluorophenyl), fluorobromophenyl (e.g. 2-fluoro-4-bromophenyl), methylenedioxychlorophenyl (e.g. 2-chloro-4,5-methylenedioxyphenyl), methoxychlorophenyl (e.g. 3-chloro-4-methoxyphenyl), methoxybromophenyl (e.g. 2-methoxy-5-bromophenyl or 3-bromo-4-methoxyphenyl), methoxynitrophenyl (e.g. 2-methoxy-5-nitrophenyl or 4-methoxy-3-nitrophenyl), ethoxynitrophenyl (e.g. 4-ethoxy-3-nitrophenyl), ethoxychlorophenyl (e.g. 4-ethoxy-3-chlorophenyl), ethoxybromophenyl (e.g. 4-ethoxy-3-bromo phenyl), benzyloxyphenyl (e.g. p-benzyloxyphenyl), phenylphenyl (e.g. p-phenylphenyl) or methylenedioxyphenylphenyl (e.g. 3,4-methylenedioxyphenylphenyl).

The cycloalkyl group suitably has 3 to 6 carbon atoms; preferably it is cyclopropyl, cyclopentyl, cyclohexyl or methylcyclohexyl.

Preferably the haloalkyl group contains 1 to 3 halogen atoms; examples are 2-chloroethyl, trifluoromethyl or trichloromethyl.

The halogen can be fluorine, chlorine, bromine or iodine.

A particular preferred compound according to the present invention has the structure:

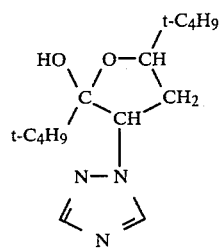

Suitable salts are salts with inorganic or organic acids, e.g. hydrochloric, nitric, sulphuric, toluenesulphonic, acetic or oxalic acid. The esters are suitably alkanoates (e.g. acetates) and the ethers are suitably alkyl (e.g. methyl or ethyl), aryl (e.g. phenyl) or aralkyl (e.g. benzyl) esters.

The metal complex is suitably one including copper, zinc, manganese or iron. The metal complexes of the compounds of general formula (I) can be prepared from the latter in known manner. For example, the complexes can be made by reacting the uncomplexed compound with a metal salt in a suitable solvent.

The compounds of the invention may be made by reacting a keto oxime of formula (I)

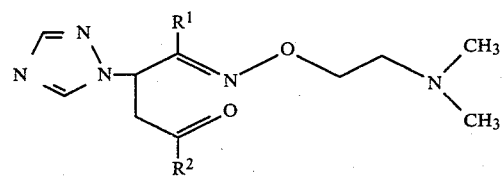

wherein $R^1$ and $R^2$ are as defined above with for example a metal hydride reducing agent (e.g. lithium aluminium hydride, sodium borohydride or aluminium isopropoxide) in an inert polar solvent (e.g. water or ethanol) and deprotecting the oxime alcohol of formula (II) formed with dilute mineral acid (e.g. hydrochloric or sulphuric acid).

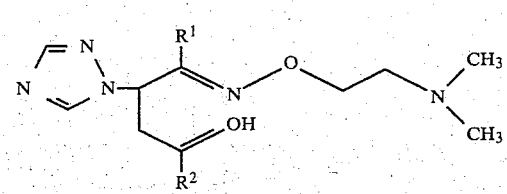

The keto alcohols of formula (III) so formed exist as the hemiacetals of formula (IV) which are the title compounds of the invention.

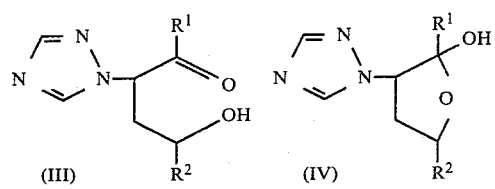

The 1,2,4-triazol-1-yl keto oximes of formula (I) are made by adding 1,2,4-triazole to an ene keto oxime of formula (V) in an appropriate solvent (e.g. refluxing toluene)

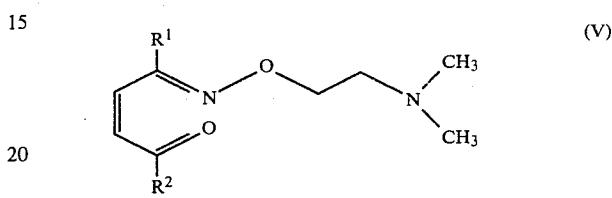

The ene keto oximes of formula (V) used as starting material are prepared by reacting the appropriate ene diketone of formula (VI) with an equivalent of N,N-dimethyl amino ethyl hydroxylamine (obtained by literature procedures Chem. Abs. 1967, 66, 1112OX (U.S. Pat. No. 3,271,428) and Chem. Abs. 1961, 8434h (British Pat. No. 842,068).

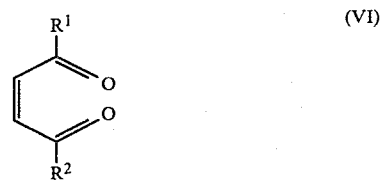

The compounds are active fungicides, particularly against the diseases:

Pyricularia oryzae on rice,

Puccinia recondita, Puccinia striiformis and other rusts on wheat, Puccinia hordei, Puccinia striiformis and other rusts on barley, and rusts on other hosts e.g. coffee, apples, vegetables and ornamental plants Erysiphe graminis (powdery mildew) on barley and wheat and other powdery mildews on various hosts such as Helminthosporium spp. on cereals, Sphaerotheca fuliginea on cucurbits (e.g., cucumber), Podosphaera leucotricha on apples and Uncinula necator on vines Cercospora arachidicola on peanuts and other Cercospora species on for example sugar beet, bananas and soya beans Botrytis cinerea (grey mould) on tomatoes, strawberries, vines and other hosts Venturia inaequalis (scab) on apples Some of the compounds have also shown a broad range of activities against fungi in vitro including Colletotrichum musae spores. They have activity against various post-harvest diseases on fruit (e.g. Penicillium digatatum and italicum on oranges and Gloeosporium musarum on bananas). Further some of the compounds are active as seed dressings against: Fusarium spp., Septoria spp., Tilletia spp. (i.e. bunt, a seed borne disease of wheat), Ustilago spp., Helminthosporium spp. on cereals, Rhizoctonia solani on cotton and Corticium sasakii on rice.

The compounds of the invention and functional derivatives, esters, ethers, salts, metal complexes and isomers thereof may be effectively used for application to the foliage of plants by spraying and other techniques. They also show acropetal systemic movement in plants, that is they have a capacity to move from root or seed through stem and shoot to leaves and other aerial parts. The compounds of the invention, and functional derivatives, esters, ethers, salts, metal complexes and isomers thereof are therefore useful as seed dressings or for soil (in furrow) application.

They also variously display plant growth regulating activity.

The compounds may be used as such for fungicidal and plant growth regulating purposes but are more conveniently formulated into compositions for such usage.

The invention therefore further provides a composition for the foregoing uses comprising as an active ingredient, a compound of general formula (I) as hereinbefore defined, or an ester, ether, acid addition salt, or metal complex of such a compound; or any isomer thereof; and a carrier or diluent for the active ingredient.

The invention also provides a method of combating fungal and bacterial diseases in, or regulating the growth of, plants, which method comprises applying to a plant, to seed of a plant, or to the locus of a plant or seed, a compound of general formula (I) as defined above; or an ester, ether, acid addition salt or metal complex of such a compound; or any isomer of any of the foregoing.

The compounds, salts, complexes, ethers and esters etc., can be applied in a number of ways, for example they can be applied, applied, formulated or unformulated, directly to the foliage of a plant, or they can be applied also to bushes and trees, to seeds or to other media in which plants, bushes or trees are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal and bactericidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, keiselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising the compound of general formula (I) or a salt, metal complex, ether or ester; or any isomer of any of the foregoing.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecylbenzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal or compounds having herbicidal, plant growth regulating or insecticidal activity.

The other fungicidal compound can be for example one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compounds are imazalil, benomyl, carbendazim (BCM), thiophanate-methyl, captafol, captan, sulphur, dithiocarbamates, carbathiins, copper oxychloride, triforine, dodemorph, tridemorph, dithianon, pyrazophos, binapacryl, quinomethionate, panoctine, furalaxyl, aluminium trio(ethyl phosphonate), DPX3217, ethirimol, dimethirimol, bupirimate, chlorothalonil and metaxanine.

The compounds of general formula (I) can be mixed with soil, peat or other rooting media for the protection of plants against seed-borne, soil-borne or foliar fungal diseases.

The following Examples illustrate the invention; the temperatures are given in degrees Centigrade (°) and percentages are on a weight basis.

EXAMPLE 1

This Example illustrates the preparation of the compound having the structure:

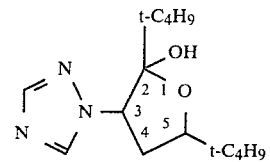

and chemical name 3-(1,2,4-triazol-1-yl)-2,5-di-t-butyl-2-hydroxy-tetrahydrofuran.

Stage 1 The Preparation of 2,2,7,7-tetramethyl-oct-4-en-3,6-dione (m.p. 107°–109°).

This compound was prepared according to the method of Ramasseul and Rassat, Bull. Soc. Chim. Fr., 1963, p 2214–2217.

Stage 2

In this process stage 2,2,7,7-tetramethyl-oct-4-en-3,6-dione (0.01 mole) and N,N-dimethyl amino ethyl hydroxylamine hydrochloride (0.01 mole) were refluxed in ethanol (75 ml) containing pyridine (5 ml) for 16 hours. The ethanol was removed in vacuo and the residue acidified with dilute hydrochloric acid and extracted with chloroform (100 ml). Removal of the solvent gave a white solid which recrystallised from petroleum ether/chloroform to give compound (V) as the HCl salt m.p. 159°–160°. Washing the HCl salt with a saturated solution of sodium bicarbonate and extracting with ether gave (V) wherein $R^1=R^2=$t-$C_4H_9$ as an oil after removing the solvent in vacuo.

Stage 3

1,2,4-Triazole (2.0 g) was refluxed with (V) wherein $R^1=R^2=$t-$C_4H_9$ (1.5 g) in toluene (50 ml) for 48 hours. The toluene was removed in vacuo and the residue purified by preparative thin layer chromatography (silica eluted with ethyl acetate) to give (I) wherein $R^1=R^2=$t-$C_4H_9$ as an oil.

Stage 4

Compound I wherein $R^1=R^2=$t-$C_4H_9$ (0.5 g) was dissolved in methanol (15 ml) and cooled to 0° C. Sodium borohydride (0.02 g) was added and the solution stirred for 3 hours at 0° C. Water (50 ml) was added, extracted with ether (50 ml) and dried over anhydrous sodium sulphate. Removal of the solvent gave compound (II) wherein $R^1=R^2=$t-$C_4H_9$ as an oil.

Stage 5

The compound (II) wherein $R^1=R^2=$t-$C_4H_9$ (0.5 g) was dissolved in ether (100 ml) and a solution of concentrated hydrochloric acid (3 ml) and 40% formaldehyde (3 ml) added. Heated on a steam bath for 1½ hours. After cooling to room temperature sodium bicarbonate solution was added and the ether layer washed with water (2×50 ml) and dried over sodium sulphate. Removal of the solvent in vacuo gave a white solid which recrystallised from (60–80) petroleum ether as the titled compound m.p. 48°–49°.

EXAMPLE 2

An emulsifiable concentrate was made up by mixing the ingredients, and stirring the mixture until all the constituents were dissolved.

| | |
|---|---|
| Compound of Example 1 | 10% |

|  |  |
|---|---|
| Ethylene dichloride | 40% |
| Calcium dodecylbenzenesulphate | 5% |
| "Lubrol" L | 10% |
| "Aromasol" H | 35% |

EXAMPLE 3

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44-100, to obtain the desired size of grains.

|  |  |
|---|---|
| Compound of Example 1 | 50% |
| "Dispersol" T | 25% |
| "Lubrol" APN 5 | 1.5% |
| Sodium acetate | 23.5% |

EXAMPLE 4

The ingredients were all ground together to produce a powder formulation readily dispersible in liquids.

|  |  |
|---|---|
| Compound of Example 1 | 45% |
| "Dispersol" T | 5% |
| "Lissapol" NX | 0.5% |
| "Cellofas" 3600 | 2% |
| Sodium acetate | 45.5% |

EXAMPLE 5

The active ingredient was dissolved in a solvent and the resultant liquid was sprayed on to the granules of China clay. The solvent was then allowed to evaporate to produce a granular composition.

|  |  |
|---|---|
| Compound of Example 1 | 5% |
| China clay granules | 95% |

EXAMPLE 6

A composition suitable for use as a seed dressing was prepared by mixing the three ingredients.

|  |  |
|---|---|
| Compound of Example 1 | 50% |
| Mineral oil | 2% |
| China clay | 48% |

EXAMPLE 7

A dusting powder was prepared by mixing the active ingredient with talc.

|  |  |
|---|---|
| Compound of Example 1 | 5% |
| Talc | 95% |

EXAMPLE 8

A Col formulation was prepared by ball-milling the constituents set out below and then forming an aqueous suspension of the ground mixture with water.

|  |  |
|---|---|
| Compound of Example 1 | 40% |
| "Dispersol" T | 10% |
| "Lubrol" APN5 | 1% |
| Water |  |

EXAMPLE 9

A dispersible powder formulation was made by mixing together the ingredients set out below and then grinding the mixture until all were thoroughly mixed.

|  |  |
|---|---|
| Compound of Example 1 | 25% |
| "Aerosol" OT/B | 2% |
| "Dispersol" A.C. | 5% |
| China clay | 28% |
| Silica | 40% |

EXAMPLE 10

This Example illustrates the preparation of a dispersible powder formulation. The ingredients were mixed and the mixture then ground in a comminution mill.

|  |  |
|---|---|
| Compound of Example 1 | 25% |
| "Perminal" BX | 1% |
| "Dispersol" T | 5% |
| Polyvinylpyrrolidone | 10% |
| Silica | 25% |
| China clay | 34% |

EXAMPLE 11

The ingredients set out below were formulated into a dispersible powder by mixing then grinding the ingredients.

|  |  |
|---|---|
| Compound of Example 1 | 25% |
| "Aerosol" OT/B | 2% |
| "Dispersol" A | 5% |
| China clay | 68% |

In Examples 2 to 11 the proportions of the ingredients given are by weight.

There now follows an explanation of the compositions or substances represented by the various Trade Marks and Trade Names mentioned above.

| | |
|---|---|
| LUBROL L: | a condensate of nonyl phenol (1 mole) with ethylene oxide (13 moles) |
| AROMASOL H: | a solvent mixture of alkylbenzenes |
| DISPERSOL T & AC: | a mixture of sodium sulphate and a condensate of formaldehyde with sodium napthalene sulphonate |
| LUBROL APN5: | a condensate of nonyl phenol (1 mole) with naphthalene oxide (5.5 moles) |
| CELLOFAS B600: | a sodium carboxymethyl cellulose thickener |
| LISSAPOL NX: | a condensate of nonyl phenol (1 mole) with ethylene oxide (8 moles) |
| AEROSOL OT/B: | dioctyl sodium sulphosuccinate |
| PERMINAL BX: | a sodium alkyl naphthalene sulphonate |

EXAMPLE 12

The compound of Example 1 was tested against a variety of foliar fungal diseases of plants grown in John Innes Potting Compost (No. 1 or 2) in 4 cm diameter minipots. A layer of fine sand was placed at the bottom of the pots containing the dicotyledonous plants to facilitate the uptake of test compound by the roots. The test compounds were formulated either by bead-milling with aqueous 'Dispersol' T or as a solution in acetone or acetone/ethanol which was diluted to the required concentration immediately before use. Suspensions were sprayed on to the foliage or applied to the roots of the same plant via the soil. Sprays were applied to maximum retention. Tween 20, to give a final concentration of 0.05% was added when the sprays were applied to cereals.

The compound was applied to the soil (roots) and to the foliage (by spraying) one or two days before the plant was inoculated with the diseases. After inoculation, the plants were put into an appropriate environment to allow infection to take place and then incubated until the disease was ready for assessment. The period between inoculation and assessment varied from four to fourteen days according to the disease and environment.

The disease control was recorded by the following grading:
4 = No disease
3 = 0–5% disease
2 = 6–25% disease
1 = 26–60% disease
0 = >60% disease
The results are shown in the Table.

TABLE

| Compound | Erysiphe graminis hordei | | Erysiphe graminis tritici | | Puccinia Recondita | | Botrytis cinerea | | Cercospora Arachidicola | |
|---|---|---|---|---|---|---|---|---|---|---|
| | Spray (5ppm) | Root Drench (5ppm) | Spray (5ppm) | Root Drench (5ppm) | Spray (10ppm) | Root Drench (10ppm) | Spray (25ppm) | Root Drench (25ppm) | Spray (25ppm) | Root Drench (25ppm) |
| Compound of Example 1 | 4 | 4 | 1 | 4 | 0 | 3 | 2 | 3 | 4 | 3 |

We claim
1. A compound having the formula:

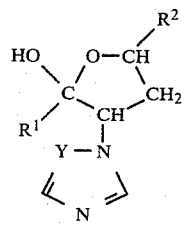

wherein each of $R^1$ and $R^2$, which may be the same or different, is unsubstituted cycloalkyl of from 3 to 6 carbon atoms or such cycloalkyl substituted with alkyl group of from 1 to 5 carbon atoms; or unsubstituted alkyl of from 1 to 5 carbon atoms or such alkyl substituted with from 1 to 3 halogen atoms; or unsubstituted phenyl or phenyl substituted with halogen or alkyl, alkoxy, haloalkyl, or hydroxyalkyl of from 1 to 4 carbon atoms, phenyl, halophenyl, cycloalkyl of from 3 to 6 carbons, nitro, cyano, hydroxy, amino, phenoxy or benzyloxy, Y is =N—; and alkanoate ester, alkyl, aryl or aralkyl ethers, acid addition salts and copper, zinc, manganese or iron complexes thereof.

2. The compound having the structure:

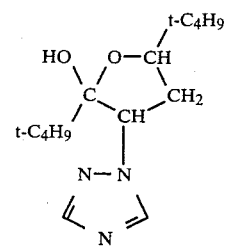

3. A process for making a compound as claimed in claim 1 which comprises reacting a keto oxime of formula

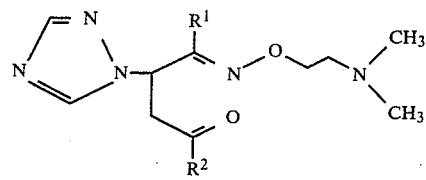

wherein $R^1$ and $R^2$ are as defined with a reducing agent in an inert polar solvent, to produce an oxime alcohol of formula

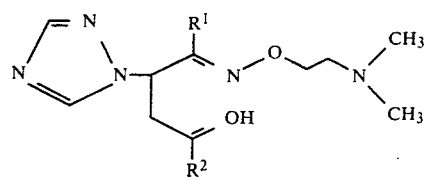

which is then deprotected by treatment with a dilute mineral acid.

4. A process as claimed in claim 3 wherein the starting 1,2,4-triazol-1-yl keto oxime is prepared by adding 1,2,4-triazole to an ene keto oxime of formula

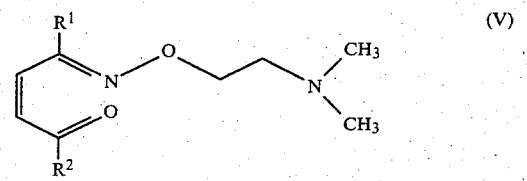

in an appropriate solvent; the ene keto oxime of the above formula used as starting material being itself prepared by reacting the appropriate ene diketone of formula

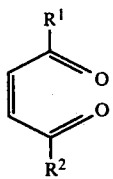 (VI)

with an equivalent of N,N-dimethyl amino ethyl hydroxylamine.

5. A composition for combating fungi and regulating plant growth comprising as an active ingredient, an effective amount of a compound as claimed in claim 1 and a carrier for the active ingredient.

6. A method of combating fungal and bacterial diseases in, or regulating the growth of, plants, which method comprises applying to a plant, to seed of a plant, or to the locus of a plant or seed, an effective amount of a compound as claimed in claim 1.

7. A method of combating fungal and bacterial diseases in, or regulating the growth of, plants, which method comprises applying to a plant, to seed of a plant, or to the locus of a plant or seed, an effective amount of a compound as claimed in claim 2.